(12) United States Patent
Roberts

(10) Patent No.: US 10,323,211 B2
(45) Date of Patent: Jun. 18, 2019

(54) METHOD FOR CULTIVATION OF HYBRID MINT PLANT DESIGNATED 13-S12-2 FOR PRODUCTION OF ESSENTIAL OIL COMPOSITION

(71) Applicant: Essex Laboratories, LLC, Napavine, WA (US)

(72) Inventor: Donald D. Roberts, Independence, OR (US)

(73) Assignee: Essex Laboratories, LLC, Napavine, WA (US)

( * ) Notice: Subject to any disclaimer, the term of this patent is extended or adjusted under 35 U.S.C. 154(b) by 0 days.

(21) Appl. No.: 15/595,827

(22) Filed: May 15, 2017

(65) Prior Publication Data
US 2017/0362535 A1    Dec. 21, 2017

Related U.S. Application Data

(63) Continuation-in-part of application No. 14/999,750, filed on Jun. 21, 2016, now Pat. No. Plant 28,363.

(51) Int. Cl.
| | |
|---|---|
| *C11B 9/00* | (2006.01) |
| *A61K 8/00* | (2006.01) |
| *C11B 9/02* | (2006.01) |
| *A01H 4/00* | (2006.01) |
| *A01H 5/12* | (2018.01) |
| *A01C 14/00* | (2006.01) |
| *A01G 22/00* | (2018.01) |
| *A01H 1/02* | (2006.01) |

(52) U.S. Cl.
CPC .............. *C11B 9/027* (2013.01); *A01C 14/00* (2013.01); *A01G 22/00* (2018.02); *A01H 1/02* (2013.01); *A01H 4/005* (2013.01); *A01H 5/12* (2013.01)

(58) Field of Classification Search
CPC ......... C11B 9/027; A01C 14/00; A01H 4/005; A01H 5/12; A01G 1/001
USPC ....................................................... 512/5, 1
See application file for complete search history.

(56) References Cited

U.S. PATENT DOCUMENTS

| | | | |
|---|---|---|---|
| PP9,197 P * | 7/1995 | Westerfield | |
| 2005/0044600 P1 * | 2/2005 | Khanuja | ................. A01H 5/12 |
| 2005/0150027 P1 | 7/2005 | Khanuja | |
| 2014/0223625 P1 | 8/2014 | Roberts | |
| 2017/0245520 A1 * | 8/2017 | Johnson | ................. A24B 15/00 |

OTHER PUBLICATIONS

Schmidt et al. "Chemical composition, olfactory evaluation and antioxidant effects of essential oil from Mentha x piperita", Natural Product Communicat, Natural Product Inc., US, vol. 4, No. 8, Jan. 1, 2009, 6 pages.
International Search Report and Written Opinion for International Patent Application No. PCT/US2017/032729, dated Jul. 24, 2017, 17 pages.

* cited by examiner

*Primary Examiner* — Jessica Whiteley
(74) *Attorney, Agent, or Firm* — Armstrong Teasdale LLP

(57) ABSTRACT

A hybrid mint plant characterized by an essential oil composition profile, methods of cultivating the hybrid mint plant, and methods of producing an essential oil composition with the essential oil composition profile using the hybrid mint plant are disclosed.

20 Claims, 5 Drawing Sheets

METHOD FOR CULTIVATION OF HYBRID MINT PLANT DESIGNATED 13-S12-2 FOR PRODUCTION OF ESSENTIAL OIL COMPOSITION

CROSS-REFERENCE TO RELATED APPLICATION

This application is a continuation in part of U.S. Plant Application No. Ser.14/999,750 filed Jun. 21, 2016, which is incorporated herein in its entirety.

BACKGROUND

The industrial mint crops are widely cultivated for the commercial production of essential oils. Mint family species (*Mentha* spp. L.), including peppermint and spearmint, are important specialty crops valued for the essential oils produced in trichomes on the surface of leaves. Spearmint is particularly known as a major source of carvone-rich essential oil for perfumery and flavoring industries and is grown worldwide. Spearmint is a fast-growing perennial crop capable of biosynthesizing significant amounts of essential oils containing a variety of ingredients, such as rosmarinic acid and other phenolics. For example, the essential oil of *Mentha arvensis* Linn. var Piperascens is a well-known source of the monoterpene 'menthol' used in the cosmetics, pharmaceutical, food, confectionery and liquor industries.

Different varieties of a given plant species may provide different ratios of ingredients within the essential oils they produce. Different mint plant species and even different varieties of the same mint plant species provide different essential oil compositions that may vary widely. However, once a particular mint plant variety is identified, the plant may be clonally propagated and used to produce essential oils of a consistent content profile for a sustained period over at least several harvests.

Mint plants are capable of producing underground rhizomes which can be used as propagates for field planting. Mint plants are also capable of rapidly producing rooted branches which can aid in faster propagations. In addition, mint plants are typically easy to cultivate, can sustain several harvests annually, and exhibit rapid re-growth after each harvest, making mint plants amenable to methods of producing essential oils of a consistent composition on an industrial scale.

SUMMARY

In one aspect, a method of producing an essential oil is provided. The method includes extracting the essential oil from a hybrid mint plant known as 13-S12-2. The essential oil includes an essential oil profile selected from the group consisting of: (a) 1-carvone and d-limonene and wherein the weight ratio of 1-carvone to d-limonene ranges from about 0.83:1 to about 1.25:1; (b) from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole; (c) from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole; and (d) from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and (e) about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

In another aspect, a method of cultivating a hybrid mint plant known as 13-S12-2 is provided. The method includes asexually propagating tip cuttings or stolon cuttings. The hybrid plant includes an essential oil. The essential oil includes an essential oil profile selected from the group consisting of: (a) 1-carvone and d-limonene and wherein the weight ratio of 1-carvone to d-limonene ranges from about 0.83:1 to about 1.25:1; (b) from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole; (c) from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole; and (d) from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and (e) about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

In another aspect, a hybrid mint plant known as 13-S12-2 is provided. The hybrid mint plant includes an essential oil. The essential oil includes an essential oil profile selected from the group consisting of: (a) 1-carvone and d-limonene and wherein the weight ratio of 1-carvone to d-limonene ranges from about 0.83:1 to about 1.25:1; (b) from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole; (c) from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole; and (d) from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and (e) about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

BRIEF DESCRIPTION OF THE DRAWINGS

The following figure illustrates various aspects of the disclosure.

Figure 1:
FIG. 1 an image of a mint plant according to one aspect of the disclosure.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, a hybrid mint plant designated 13-S12-2, methods of cultivating the hybrid mint plant, and methods of producing an essential oil using the hybrid mint plant are provided.

I. Taxonomic Description

The hybrid mint plant designated 13-S12-2 has a taxonomic description of *Mentha×gracilis* (syn. *Mentha×gentilis* L.; syn. *Mentha cardiac* (S. F. Gray) Bak.). The hybrid mint plant is also identified as 'Jefferson Mint'.

The hybrid mint plant identified as 'Jefferson Mint', under greenhouse and field growing conditions, is a bush-type plant with lateral branches at each node of the main stems. The height of 'Jefferson Mint' is slightly less than 'Native Spearmint' growing under similar conditions and will vary based on fertilizer, soil quality, and water application, amongst other known factors that affect growth patterns. 'Jefferson Mint' is typically ranges from about 0.3 m to about 0.5 m at mid-stem in width and ranges from about 0.9 m to about 1.2 m min height under greenhouse environmental conditions. Field grown 'Jefferson Mint' has a width ranging from about 0.3 m to about 0.5 m at mid-stem and has a height ranging from about 0.8 m to about 1.2 m. Secondary and tertiary branching occurs to form a compact growth habit. When 'Jefferson Mint' is mature and ready for harvest, the main stem at mid-plant (approximately between the eleventh and twelfth node) ranges from about 4.9 mm to about 7.9 mm in width. The secondary and tertiary branch stems range in width from about 2.5 mm to about 2.7 mm, and from about 1.1 to about 1.3 mm, respectively. The stems are square, glabrous, and possess a green color that matches The Fifth Edition Royal Horticultural Society Colour Chart 138A green group.

Mature leaves on 'Jefferson Mint' are lanceolate. The adaxial leaf surface is sparsely hairy. The abaxial leaf surface is sub-glabrous with oil glands distributed across the surface. Mid-main stem leaf size at flowering ranges from about 27 mm to about 31 mm in width and ranges from about 49 mm to about 53 mm in length. Leaf size on secondary branches at flowering ranges from about 17 mm to about 21 mm in width and ranges from about 31 mm to about 39 mm in length. Leaf petioles on the main stem leaves range from about 4.3 mm to about 7.1 mm in length, while petioles on secondary branch stem leaves are 1.6 mm in length. Leaves on the mid-main stem are dentate. The main stem leaves are toothed having a number of teeth ranging from about 8 teeth to about 9 teeth on each side. Secondary branch leaves have about 2 teeth on each side. The abaxial leaf is dark green in color, ranging from The Fifth Edition Royal Horticultural Society Colour Chart 138A in the green group classification. The leaf has a number of lateral veins ranging in number from about 6 veins to about 8 veins. All lateral veins are more or less aligned in parallel off the main vein that runs from the petiole to the tip of the leaf. The veins are prominent in all leaves of 'Jefferson Mint.'

The inflorescence of 'Jefferson Mint' is a cylindrical spike with capitate flowers developing at the nodes of the stem. The capitate flowers range in width from about 12 mm to about 13 mm and are about 6 mm in length. The flowers consist of five petals fused into a two-lipped corolla. The corolla is light in color as illustrated in The Fifth Edition Royal Horticultural Society Colour Chart NN155D in the white group. The calyx is generally yellow-green and is 143A of The Fifth Edition Royal Horticultural Society Colour Chart, green group. The gynoecium consists of a single pistil with two lobed stigma that is exserted. The androecium consists of four stamens, each with a distinct filament and anther.

II. Essential Oil Composition

In various aspects, the hybrid mint plant designated 13-S12-2 contains an essential oil that may be extracted using an extraction method as described below. The essential oil is contained in at least one part of the hybrid mint plant or any portion thereof. Non-limiting examples of parts of the hybrid mint plant that may contain the essential oil include a leaf, a stem, a seed, a rhizome, a stolon, and/or a flower.

In one aspect, the essential oil includes 1-carvone, d-limonene, 3-octonol, dihydrocarvone, menthone, and 1,8-cineole. In another aspect, the 1-carvone and d-limonene in the essential oil has a weight ratio ranging from about 0.83:1 to about 1.25:1. In an additional aspect, the essential oil includes from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole. In another additional aspect, the essential oil includes from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole. In yet another additional aspect, the essential oil includes from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole. In one additional aspect, the essential oil includes about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

In another aspect, the essential oil includes about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole In one aspect, the yield of essential oil extracted from the hybrid mint plant may vary without changing the essential oil profile, defined herein as the relative amounts of each of the ingredients within the essential oil extracted from the hybrid mint plant. In another aspect, delaying harvest of the hybrid mint plant increases the yield of essential oil without significantly changing the essential oil profile. 'Jefferson Mint' is quite hardy; and yields well, similar to the essential oil yield for other *Mentha arvensis* varieties, as do some other spearmints, and yield of essential oil that is significantly higher than the corresponding essential oil yield for Black Mitcham (*Mentha piperata*).

Without being limited to any particular theory, it is thought that the essential oil profile may vary due to individual differences in any one or more of at least several factors including, but not limited to, environmental factors and the part of the hybrid mint plant from which the essential oil is extracted. Non-limiting examples of environmental factors that may impact the essential oil profile include water, sunlight, latitude and day length, nutrients, planting density, microbial infections, and herbivorous organisms including insects. In one aspect, plant stress caused by a deficiency in an environmental factor such as water or nutrients may cause a variation in the essential oil profile. In various aspects, the variation in any one or more of the ingredients within the essential oil may vary by no more than 20%, no more than 10%, no more than 5%, no more than 2%, or no more than 1% relative to a characteristic essential oil profile, including, but not limited to, the essential oil profile for the 'Jefferson Mint' summarized in Table 1 below.

In various aspects, the essential oils produced using the disclosed methods are suitable for incorporation into a plurality of preparations including, but not limited to: cosmetic preparations, flavor preparations, pharmaceutical preparations, food preparations, tea preparations, air care products, and fragrance preparations.

Non-limiting examples of cosmetic preparations include skin care products, hair care products, personal hygiene products, sun protection products, and oral and dental care products. Non-limiting examples of a skin care products include soaps, lotions, body washes, bath gels, deodorants, antiperspirants, fragrances, perfumes, cosmetics or combinations thereof, such as antiperspirant/deodorants (ABDO). Non-limiting examples of hair care products include shampoos, conditioners, pomades, brilliantines, set lotions, hair sticks, hair solids, hair oils, hair treatments, hair creams, hair tonics, hair liquids, hair sprays, bandolins, hair growth agents, hair dyes, or any combination thereof. Non-limiting examples of personal hygiene products include shaving creams, shaving lotions, after shave lotions, soaps, shampoos, hair conditioners, deodorants, sun-screen products, bath salts and bath oils. Non-limiting examples of sun protection products include sunscreens, sun sticks, suntan products, after-sun treatment products, artificial tanning products, skin-whitening products, and combinations thereof. Non-limiting examples of oral and dental care products include dentifrices, mouthwashes, dental gels, lozenges, beads, gums, oral strips, mints, liquid toothpastes, sprays, paint-on gels, lip balms, whitening strips, breath strips, oral chews, and combinations thereof.

Non-limiting examples of flavor preparations include any composition added to impart or help impart a taste or aroma in food, and may be provided in a variety of forms including, but not limited to, liquid, paste, solid, in encapsulated form bound to or coated onto carriers/particles, and/or powder. Non-limiting examples of pharmaceutical preparations include skin external preparations such as cataplasma and ointments, and oral medicines. Non-limiting examples of food preparations include solid foods, liquid foods, drinks, emulsions, slurries, curds, dried food products, packaged food products, raw foods, processed foods, powders, granules, dietary supplements, edible substances/materials, chewing gums, or any combinations thereof. Non-limiting examples of tea preparations include jasmine teas black teas, oolong teas, green teas, various herbal teas, and the like. Non-limiting examples of air care products include air fresheners and scent delivery systems. Non-limiting examples of fragrance preparations include any odor-releasing composition in a form of solids, waxes, films, sheets, fabrics, meshes, sponges, powders, liquids, colloids, emulsions, creams, gels, lotions, pastes, ointments, liniments, balms, sprays, roll-ons, or any combinations thereof.

III. Method of Cultivation

In various aspects, the 'Jefferson Mint' variety is grown according to any existing mint cultivation practice without limitation. In summary, the hybrid mint plant is cultivated by selecting a hybrid mint plant for cultivation, asexually propagating tip cuttings and/or stolon cuttings from the selected hybrid mint plant, and planting the propagated tip cutting and/or stolon cuttings in a field. The hybrid mint plants in the field may be harvested repeatedly by cutting the plant above ground level, leaving a rhizome and/or stolon in the ground to grow a new mint plant for subsequent harvest in a similar manner. In another aspect, the hybrid mint plants in the field may be initially grown by germinating hybrid mint plant seeds planted in the field.

In one aspect, the hybrid mint plant is produced by cross-breeding at least two or more mint varieties using a polycross method. In the polycross method, single plants of each variety are positioned in a confined area and permitted to cross-pollinate. Any offspring plants resulting from the cross-pollination are assessed according to at least one selection factor. Non-limiting examples of suitable selection factors include plant vigor, essential oil composition profile, disease resistance, pest resistance, biomass as related to cost of distillation, concentration of essential oil, and any other suitable selection factor.

In one aspect, the vigor of an offspring plant is typically assessed in terms of one or more phenotypic traits relative to the other offspring plants. Non-limiting examples of phenotypic traits used to assess vigor include yield in biomass per plant, growth rate, time to first flowering, leaf-to-stem ratio, leaf color, leaf size, and any other phenotypic trait related to vigor.

In another aspect, disease resistance may be assessed by comparing the health of a group of offspring plants to a comparison group of plants of a known variety including, but not limited to, a commercial mint variety, that is known to be susceptible to a disease pathogen. In this assessment, both groups of plants are grown at a location and/or under conditions known to contain a pathogen, including, but not limited to, a wilt fungus or a rust fungus. In this other aspect, an offspring plant is considered to be disease resistant to a pathogen if the group of offspring plants is observed to be healthier than the comparison group of plants known to be susceptible to the disease.

A subset of the offspring plants that possess one or more selection factors are selected for further propagation. In various aspects, the subset of selected offspring plants may be about one plant, about two plants, about five plants, about ten plants, about twenty plants, about thirty plants, about fifty plants, about seventy plants, or about 100 plants. The selected offspring plants are asexually propagated to further increase the number of candidate mint hybrid plants. In an aspect, a portion of the offspring plants are selected for asexual propagation in larger fields using existing commercial mint cultivation methods. In various aspects, about 1%, about 3%, about 5%, about 7%, or about 10% of the initial offspring plant varieties are selected for commercial cultivation.

In various aspects, the commercial cultivation includes asexually propagating stem tip cuttings and/or stolon cuttings of the selected hybrid mint variety according to existing standard practices. The stem tip or stolon cuttings typically develop roots as a result of the asexual propagation and are subsequently planted in a field suitable for mint cultivation and subsequently develop into hybrid mint plants. The growth of the hybrid mint plants is encouraged by providing needed environmental factors according to standard mint cultivation practices including, but not limited to: sun exposure, water, nutrients, herbicides and/or pesticides as needed.

In an aspect, the hybrid mint plants are harvested at first flowering. In various other aspects, the hybrid mint plants are harvested when less than about 10%, least than about 20%, less than about 40%, less than about 60%, and less than about 75% of the plants exhibit flowering. Typically the hybrid mint plants are harvested at flower bloom of the plants. Without being limited to any particular theory, harvesting the hybrid mint plants prior to reproduction prevents the occurrence of seeds that may introduce variation among the genotypes of the hybrid mint plants in the field and that may further introduce variation in the essential oil composition profile characterizing the essential oils extracted from the harvested hybrid mint plants. In one aspect, essentially all hybrid mint plants harvested from the field are clones of the original hybrid mint plant selected as described above.

In one aspect, the hybrid mint plant is harvested by cutting the plant above ground level, leaving the rhizomes and/or stolons of the plant intact in the ground. In this aspect the rhizomes and/or stolons are then cultivated to produce a subsequent crop of hybrid mint plants according to existing mint cultivation practices. In one aspect, the hybrid mint plants may be repeatedly harvested in this manner to produce several crops in a growing season.

In another aspect, the rhizomes and/or stolons of the hybrid mint plant may also be removed from the soil and stored in a storage facility including, but not limited to a greenhouse or a plant nursery. In this aspect, the rhizomes and/or stolons may be propagated to develop roots and subsequently replanted in a field to produce one or more additional crops of hybrid mint plants.

In an additional aspect, the hybrid mint plants may be allowed to set seed to produce a plurality of seeds. In this aspect, the hybrid mint plants may be harvested and the seeds may be separated from the other plant parts for subsequent planting to produce a subsequent hybrid mint plant crop. In another aspect, the seeds may be retained with the rest of the harvested hybrid mint plant for further processing to remove the essential oils. In one aspect, the hybrid mint plants may be allowed to set seed after a first growing season that may include several harvests. In various other aspects, the hybrid mint plants may be allowed to set seed after a second growing season, a third growing season, or any other subsequent growing season without limitation.

In various aspects, the hybrid mint plants that were harvested by cutting above ground level may be allowed to cure for a curing period. In various aspects, the curing period may extend for at least one day, at least two days, or at least five days or more. The harvested hybrid mint plants may be cured in the field, or the harvested hybrid mint plants may be moved to another location for curing. In an aspect, the cured hybrid mint crop is subjected to extraction of the essential oils using any known extraction or distillation method including, but not limited to, steam distillation as described below.

IV. Method of Extracting Essential Oils from Hybrid Mint Plants

In various aspects, the essential oil composition is extracted from the harvested hybrid mint plants by any existing method including, but not limited to, a steam distillation process. Steam distillation of essential oil from mint plants is well-known in the art and works on the principle that steaming the cut plants encourages release of the plants' essential oils via rupture of the plant's oil sacs which are taken up with the steam.

During steam distillation, a boiler creates steam that is directed into a lower portion of a container containing plant parts of the harvested hybrid mint plants. In an aspect, the harvested hybrid mint plants are mechanically reduced in size to the plant parts by any known mechanical process including, but not limited to, shredding, chopping, crushing, macerating, and any other suitable mechanical process. The steam introduced into the lower portion of the container rises upward through the plant parts, inducing the movement of essential oil released upward from the plant parts with the steam. The steam/essential oil mixture is removed from the container via a port formed in an upper portion of the container. The steam/oil mixture removed from the container is directed through a condenser which causes the oil and water to separate, thereby allowing the essential oil to be recovered. In one aspect, the essential oil is used as recovered for a variety of purposes described above. In another aspect, the essential oil is subjected to additional processes to isolate one or more individual ingredients of the essential oil composition. Non-limiting examples of additional processes include distillation.

In various aspects, the extraction of the essential oil composition from the harvested hybrid mint plants may be performed using any suitable existing device without limitation. In one aspect, the extraction of the essential oil composition from the harvested hybrid mint plants may be performed using a portable extraction device, such as a wheeled distillation tub configured to travel throughout the field containing harvested hybrid mint plants that have been previously cured.

Figure 2:
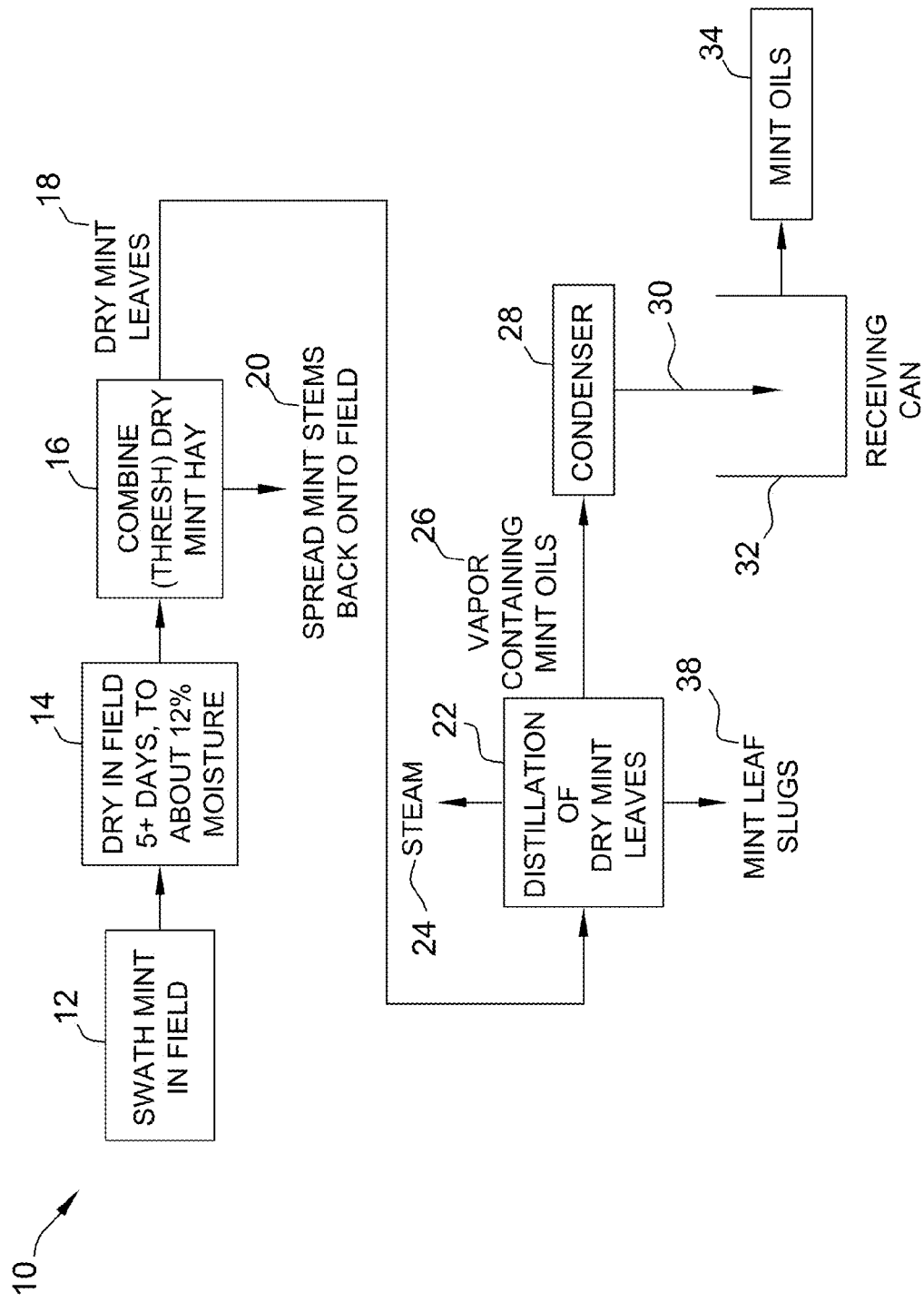
FIG. 2 is a flow chart of a mint harvest and distillation process according to one aspect of the disclosure.

By way of non-limiting example, a process 10 for extracting the essential oil from the hybrid mint plants is illustrated schematically in FIG. 2. When the growing mint crop in the field is ready for harvest, the mint plants are swathed at step 12 into windrows of mint hay in a conventional fashion according to standard mint agricultural practices. The windrowed mint hay is then left to dry at step 14 in the field until a desired moisture content is achieved. In one aspect, the windrowed mint hay is dried at step 14 for about two to three days and about 35-40% moisture content. In another aspect, the windrowed mint hay is dried at step 14 for about 5 days or more to achieve a moisture content of less than about 15%, and preferably about 12%.

The mint leaves and stems are put into the distilling tub 22 and then injected with steam 24 to begin the distillation process. Vapor 26 containing the mint oils is transferred to a condenser 28 and the condensate 30 flows to a receiving can 32 where the mint oils 34 float to the surface for decanting into a mint oil collector. Water sodden mint leaves or slugs 36 are removed for spreading back on the mint fields or for use as mulch.

In one aspect, the dried mint hay is threshed at step 16 by a combine to separate the dried mint leaves 18 from the mint stems 20. The stripped mint stems are spread by the combine back onto the field. The mint leaves are collected in the combine hopper and periodically transferred to a transport tub or truck for transfer to the distillery, or to storage for later distilling.

Figure 3A:
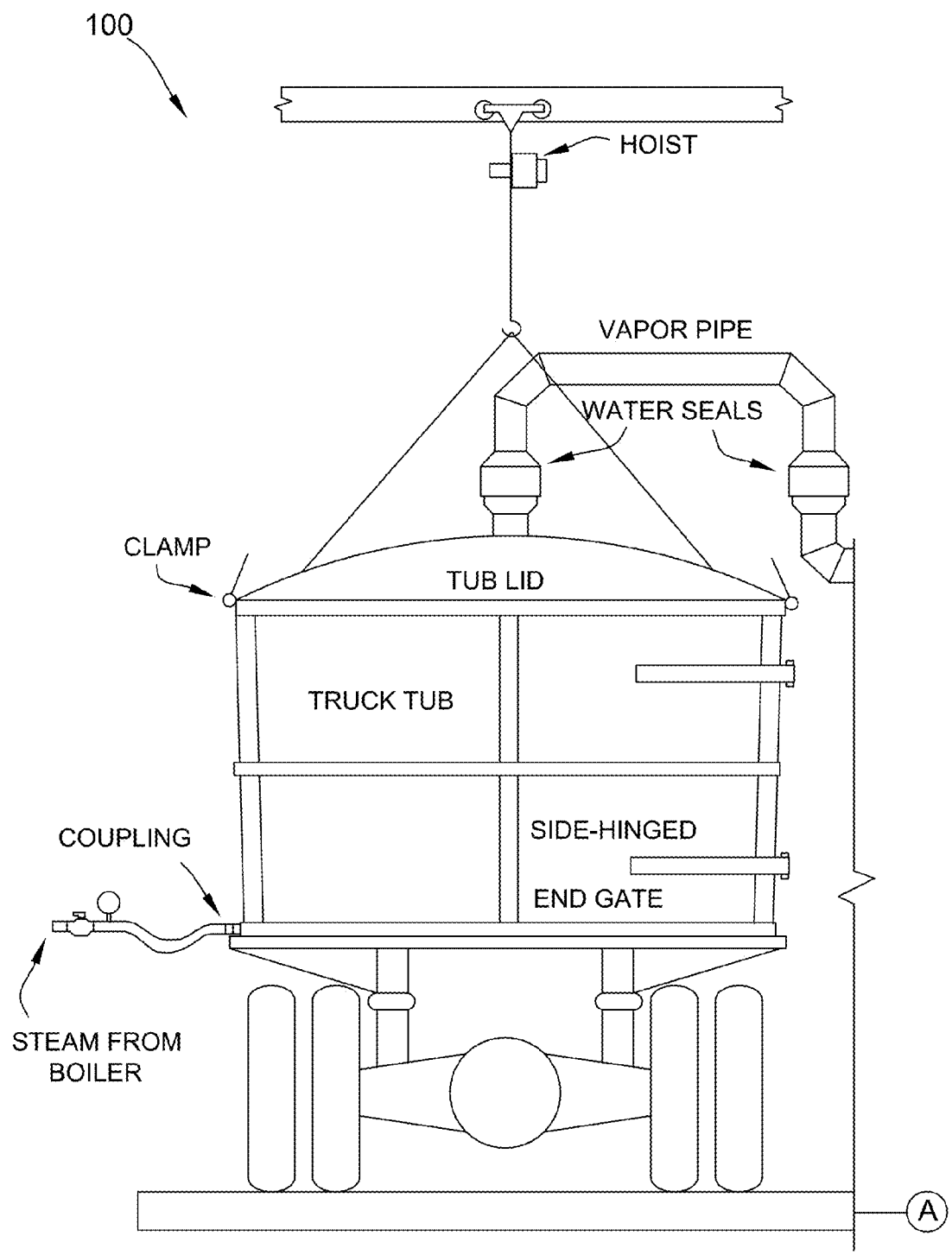
FIGS. 3A, 3B, and 3C are schematic illustrations of a steam extraction and distillation device.
Figure 3B:
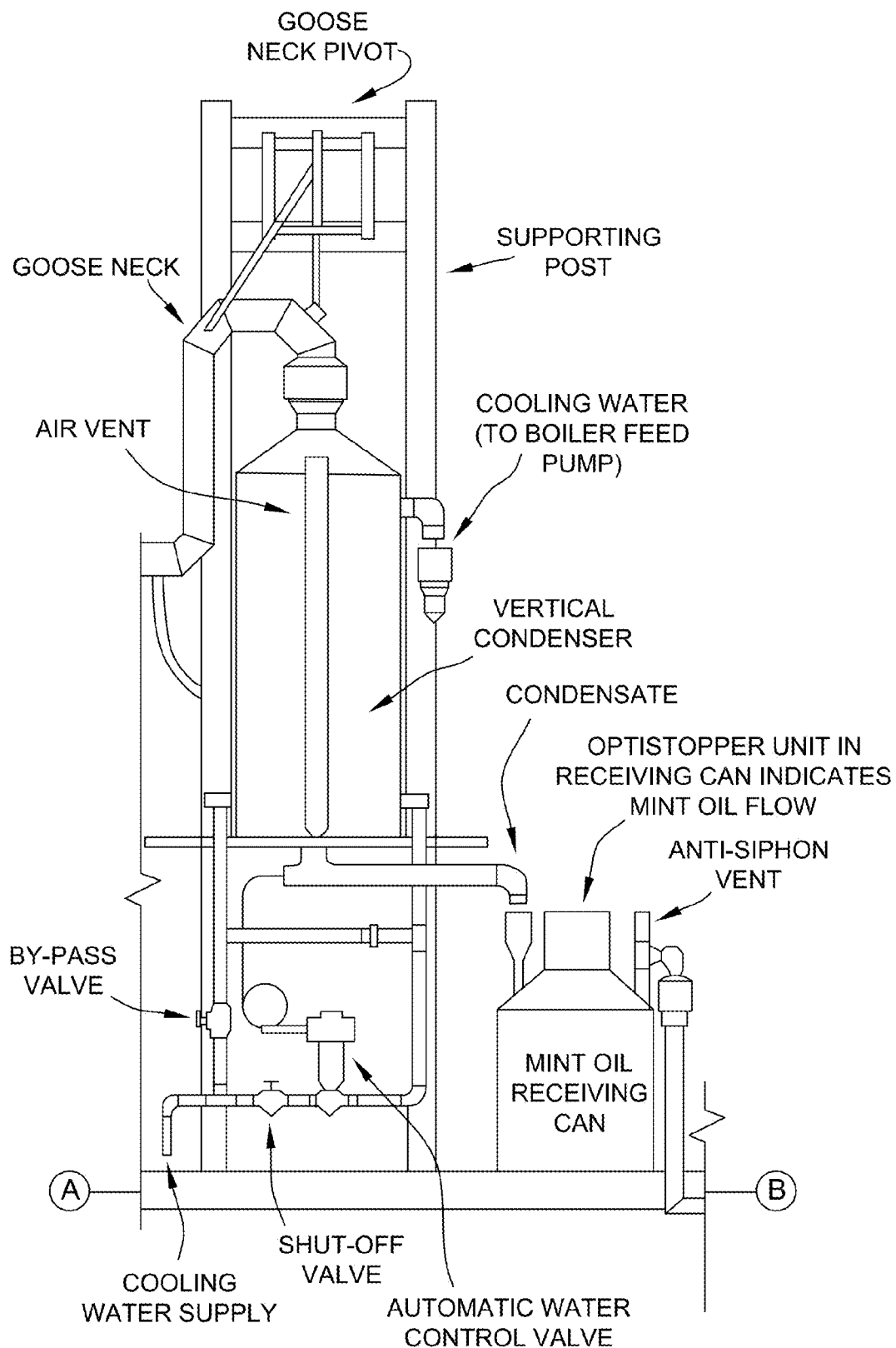
Figure 3C:
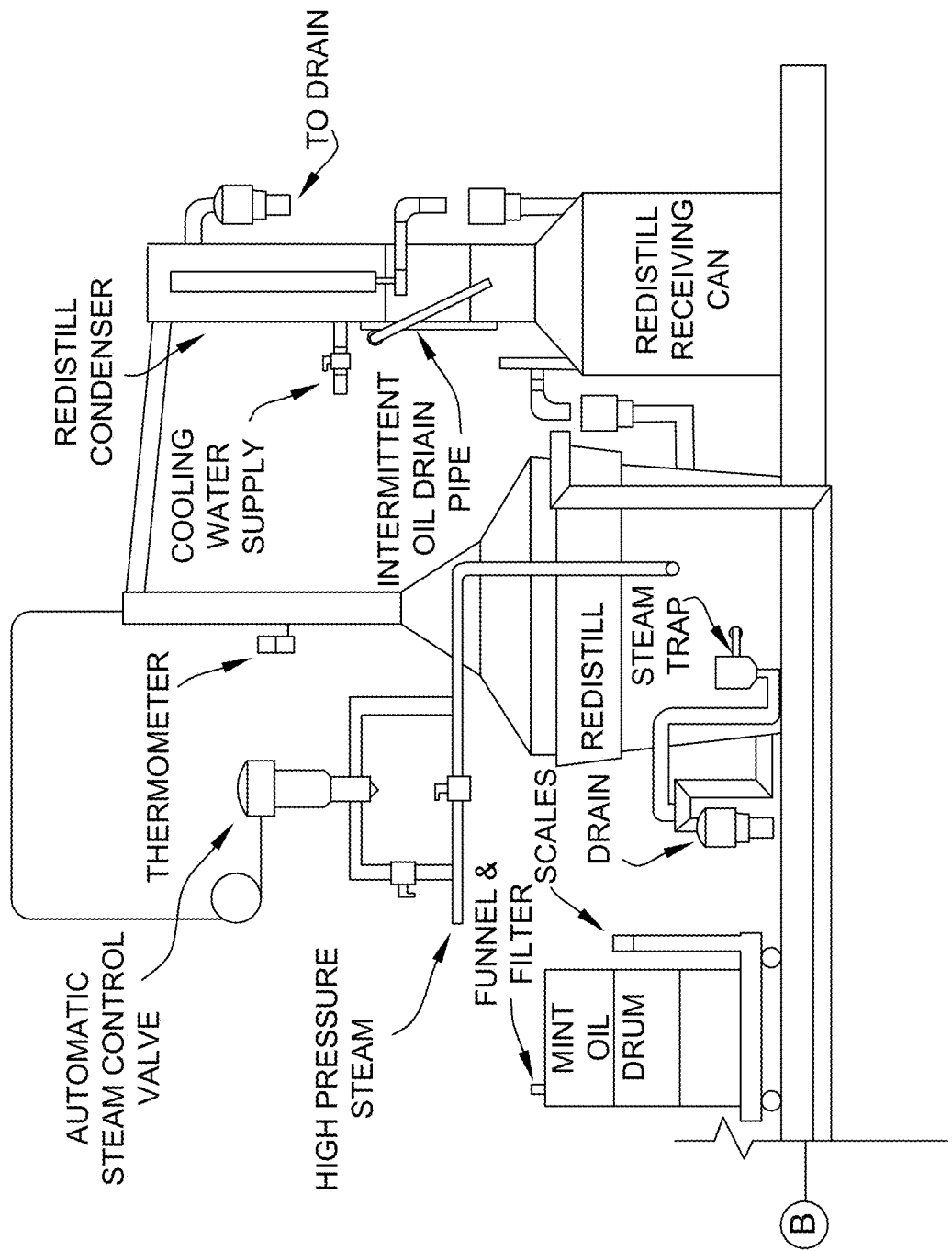

By way of non-limiting example, a steam extraction and distillation device 100 used to extract the essential oils from the harvested mint plants is illustrated schematically at FIGS. 3A, 3B, and 3C

EXAMPLES

The following examples illustrate various aspects of the disclosure.

Example 1

Selection of Hybrid Mint Plants

Candidate hybrid mint plants were produced using a polycross method. A relatively small number of single parent plants of known phenotype, such as essential oil composition profile or disease resistance were selected. The parent plants were planted in a plot and allowed to freely cross. Although not all parent plants crossed with one another, a generation of offspring resulting from the polycross event (i.e. "baby" plants) is assessed for vigor, oil chemistry and disease resistance, and individual candidate plants are selected for subsequent asexual propagation.

For a first year, the individual candidate plants were asexually propagated to produce about 25 individual clones. Those clones that did not exhibit any signs of infection were selected for additional asexual propagation until each individual candidate plant had been propagated to produce a group of 100 clones. An essential oil profile was then performed for each candidate plant, and those plants that possessed a desired profile were selected for further asexual propagation.

The asexually propagated groups of candidate plants with desirable essential oil profiles were than grown in plots of about 1 acre according to the methods described herein above. The essential oil composition of the resulting crop was assessed to determine whether the plants possessed the desired essential oil profile after field growth conditions. Standard commercial mint varieties were grown in nearby plots and the phenotypic traits of the candidate plants were compared to the corresponding phenotypic traits of the commercial mint varieties to assess vigor and/or disease resistance.

Example 2

Harvest and Essential Oil Assessment of Hybrid Mint Plants

Fields of hybrid mint plants grown as described in Example 1 were harvested at the first appearance of flowering. The plants were harvested using standard harvest techniques and equipment. The whole mint plants were cut to about 1-2 inches above soil using a swather. The cut mint plants were left to cure in windrows. Once the mint plants were dried to a desired water content, an implement was used to pick up the swathed mint plants, chop the mint plants, and blow the chopped mint plants into a distillation tub of a stationary distillery similar to the distillery described above to extract the essential oil.

The essential oil extracted in the distillery was subjected to composition analysis using a gas chromatography instrument. The percentages were determined by calculation of the relative peak areas. A similar analysis was performed on two commercial mint varieties: 'Native Spearmint' and 'Scotch Spearmint'.

Table 1 below summarizes a comparison of the components of the essential oil of 'Jefferson Mint' compared the essential oil profile of two other commercial mint varieties. The values listed in Table 1 are percentages based upon the analysis of the respective mint oils by gas chromatography. The 'Native Spearmint' and 'Scotch Spearmint' oil samples analyzed were selected to be typical of what is produced by mint growers. 'Jefferson Mint' oil samples were distilled from plants grown in test plots in the field under standard cultivation conditions and practices.

The essential oil extracted from 'Jefferson Mint' typically has similar components to the corresponding components of commercial essential oil produced by 'Native Spearmint' and 'Scotch Spearmint' mint varieties as illustrated in Table 1 below. However, the ratio of oil components differs between the commercial spearmint oil and that of 'Jefferson Mint.' The concentration of carvone in the oil of 'Jefferson Mint' is lower than that of 'Scotch Spearmint.' The amount of limonene in the oil of 'Jefferson Mint' is higher than that of 'Native' and 'Scotch Spearmint.' Organoleptically, the oil of 'Jefferson Mint' is different from that of 'Scotch Spearmint' or 'Native Spearmint' reflecting the difference in oil component ratios.

TABLE 1

Composition of 'Jefferson Mint' Essential Oil Compared to Commercial Mint Essential Oils

| Essential Oil Components | 'Jefferson Mint' | Commercial 'Native Spearmint' | Commercial 'Scotch Spearmint' |
| --- | --- | --- | --- |
| d-Limonene | 30.3 | 10.5 | 16.8 |
| 1,8-Cineole | <1.0 | 1.4 | 1.3 |
| 3-Octanol | 2.4 | 1.0 | 1.9 |
| Menthone | 1.3 | <1.0 | 1.0 |
| Dihydrocarvone | 3.0 | 1.3 | 0.9 |
| L-carvone | 31.5 | 68.8 | 69.2 |

The organoleptic properties of the 'Jefferson Mint' were also evaluated. 'Jefferson Mint' was a spearmint variety, likely more similar to 'Scotch Mint' (*Mentha cardiaca*) than Native spearmint (*Mentha spicata*). The amount of carvone in the essential oil composition was relatively low in 'Jefferson Mint', and the amount of limonene was relatively high. The presence of peppermint components in the essential oil of the 'Jefferson Mint', including menthol and menthone, were at notably higher levels in 'Jefferson Mint' than other commercial spearmints.

The sensory profile of the 'Jefferson Mint' was quite balanced given the high limonene content. The low carvone level may enable blending of 'Jefferson Mint' with higher carvone, less expensive spearmints (C-80 and terpeneless Indian *M. spicata*) to give a sweet, pleasant spearmint character.

'Jefferson Mint' had an organoleptic profile similar to 'Scotch peppermint" (i.e. *Mentha cardiac*) with a strong herbal top note along with a sweet and robust carvony note.

In addition, 'Jefferson Mint' had a sweet, balanced, anise, slightly terpenic organoleptic profile.

Example 3

Consistency of Essential Oil Profiles of Hybrid Mint Plants

To assess the consistency of the essential oil profile of the 'Jefferson Mint', the following experiments were conducted. Hybrid mint plants grown as described in Example 1 were harvested at the first appearance of flowering for the "baby" plants, as well as the first and second cuts of the second growing season. Growth of the hybrid mint variety for the second growing season was accomplished in 8 foot×32 foot plots according to standard mint agriculture practices.

At the time of each harvest, the cut mint was dried to about 40% moisture content and the essential oil was extracted using the steam extraction method as described above. Samples of the essential oils extracted from each harvest were subjected to gas chromatography measurements to assess the essential oil profiles for the different harvests, In addition, essential oil samples representative of the commercial mint species Mentha cardiac and Mentha spicata were extracted and similarly subjected to gas chromatography to obtain essential oil profiles of these mint varieties for comparison.

Table 2 is a summary of the essential oil profiles for the Jefferson Mint, the *Mentha cardiac* and *Mentha spicata*. The low and high values of any entries within Table 2 represent the lowest and highest observed values measured amongst the essential oils extracted from the three harvests.

TABLE 2

Variation in Essential Oil Profile for Three Harvests - 'Jefferson Mint'

| Essential Oil Component (%) | Jefferson Spearmint | M. cardiaca | M. spicata |
|---|---|---|---|
| alpha-pinene | 0.9-1 | | 0.4-0.8 |
| beta-pinene | 0.8-0.9 | | |
| limonene | 30-39 | 14-20 | 8-20 |
| 1,8-cineole | 0.7-0.8 | | |
| 3-octanol | 1.3-1.8 | | |
| trans-sabinene hydrate | 0.1-0.2 | 0 | 0.3-2 |
| menthone | 1.6-2.6 | 0.8-1.2 | 0-0.1 |
| menthofuran | | | |
| isomenthone | 1.5-2.3 | | |
| menthyl acetate | | | |
| isopulegol | | | |
| neomenthol | | | |
| beta-caryophyllene | | | |
| menthol | 2-5 | 0-0.1 | 0-0.1 |
| germacrene-D | 0.5-1 | | |
| piperitone | | | |
| beta-bourbonene | 0.5-1.2 | | |
| dihydrocarvone | 0.8-3 | 1-3 | 1-3 |
| carvone | 33-46 | 63-75 | 55-70 |

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosures as come within known or customary practice in the art to which the invention pertains and as may be applied to the essential features hereinbefore set forth, and as fall within the scope of the invention and the limits of the appended claim While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosures as come within known or customary practice in the art to which the invention pertains and as may be applied to the essential features hereinbefore set forth, and as fall within the scope of the invention and the limits of the appended claim.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

What is claimed is:

1. A method of producing an essential oil, the method comprising extracting the essential oil from a hybrid mint plant known as 13-S12-2, wherein the essential oil comprises an essential oil profile selected from the group consisting of:
   a. 1-carvone and d-limonene and wherein the weight ratio of 1-carvone to d-limonene ranges from about 0.83:1 to about 1.25:1;
   b. from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole;
   c. from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole;
   d. from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and
   e. about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

2. The method of claim 1, wherein the essential oil is extracted from at least one part of the hybrid mint plant or any portion thereof, the at least one part of the hybrid mint plant selected from the group consisting of a leaf, a stem, a seed, a rhizome, a stolon, a flower, and any combination thereof.

3. The method of claim 1, wherein the essential oil is extracted from the hybrid mint plant that is harvested at initial flowering.

4. The method of claim 1, further comprising cultivating the hybrid mint plant known as 13-S12-2.

5. A method of cultivating a hybrid mint plant known as 13-S12-2, the method comprising asexually propagating tip cuttings or stolon cuttings, wherein the hybrid plant comprises an essential oil, the essential oil comprising an essential oil profile selected from the group consisting of:
   a. 1-carvone and d-limonene and wherein the weight ratio of 1-carvone to d-limonene ranges from about 0.83:1 to about 1.25:1;
   b. from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole;
   c. from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole;
   d. from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and
   e. about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

6. The method of claim 5, wherein the hybrid mint plant is resistant to mint wilt caused by soil-borne *Verticillium dahaliae* fungus.

7. The method of claim 5, further comprising planting the propagated tip cuttings or stolon cuttings in a field.

8. The method of claim 5 further comprising harvesting the hybrid mint plant at first flowering.

9. The method of claim 8, wherein harvesting the hybrid mint plant at first flowering further comprises cutting and removing the hybrid mint plant above ground level, wherein a portion of the hybrid mint plant is left to propagate a subsequent crop of hybrid mint plant, the portion of the hybrid mint plant selected from a stolon, a rhizome, and any combination thereof.

10. The method of claim 9, further comprising removing the portion of the hybrid mint plant left to propagate to a storage facility, allowing the stored portion of the hybrid mint plant to develop roots, and replanting the stored portion of the hybrid mint plant.

11. The method of claim 9, wherein a portion of the hybrid mint plant is left to propagate a subsequent crop of hybrid mint plants, the portion of the hybrid mint plant selected from a stolon, a rhizome, and any combination thereof.

12. The method of claim 5, further comprising harvesting the hybrid mint plant after the hybrid mint plant produces seeds.

13. The method of claim 12, wherein harvesting the hybrid mint plant after the hybrid mint plant produces seeds further comprises cutting and removing the hybrid mint plant above ground level, wherein a portion of the hybrid mint plant is left to propagate a subsequent crop of hybrid mint plant, the portion of the hybrid mint plant selected from a stolon, a rhizome, and any combination thereof.

14. The method of claim 13, further comprising separating the seeds from the harvested hybrid mint plant.

15. The method of claim 14, further comprising removing the portion of the hybrid mint plant left to propagate to a storage facility, allowing the stored portion of the hybrid mint plant to develop roots, and replanting the stored portion of the hybrid mint plant.

16. A hybrid mint plant known as 13-S12-2, the hybrid mint plant comprising an essential oil, the essential oil comprising an essential oil profile selected from the group consisting of:
   a. 1-carvone and d-limonene and wherein the weight ratio of 1-carvone to d-limonene ranges from about 0.83:1 to about 1.25:1;
   b. from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole;
   c. from about 28% mass to about 35% mass of 1-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole;
   d. from about 30% mass to about 33% mass of 1-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and
   e. about 31.5% mass of 1-carvone, about 30.3% mass of d-limonene, about 2.4% mass of 3-octonol, about 3% mass of dihydrocarvone, about 1.3% mass of menthone, and less than about 1% of 1,8-cineole.

17. The hybrid mint plant of claim 16, further comprising at least one plant part selected from the group consisting of a leaf, a stem, a seed, a rhizome, a stolon, a flower, and any combination thereof.

18. The hybrid mint plant of claim 17, wherein the at least one plant part comprises a leaf or any portion thereof.

19. The hybrid mint plant of claim 16, wherein the hybrid mint plant is resistant to mint wilt caused by soil-borne *Verticillium dahaliae* fungus.

20. The hybrid mint plant of claim 16, wherein the essential oil comprises an essential oil profile selected from the group consisting of:
   b. from about 25% mass to about 38% mass of 1-carvone, from about 24% mass to about 37% mass of d-limonene, from about 1.9% mass to about 2.9% mass of 3-octonol, from about 2.4% mass to about 3.6% mass of dihydrocarvone, from about 1.0% mass to about 1.6% mass of menthone, and less than about 1% of 1,8-cineole;
c. from about 28% mass to about 35% mass of l-carvone, from about 27% mass to about 33% mass of d-limonene, from about 2.1% mass to about 2.7% mass of 3-octonol, from about 2.7% mass to about 3.3% mass of dihydrocarvone, from about 1.1% mass to about 1.5% mass of menthone, and less than about 1% of 1,8-cineole;
d. from about 30% mass to about 33% mass of l-carvone, from about 29% mass to about 32% mass of d-limonene, from about 2.3% mass to about 2.5% mass of 3-octonol, from about 2.8% mass to about 3.1% mass of dihydrocarvone, from about 1.2% mass to about 1.4% mass of menthone, and less than about 1% of 1,8-cineole; and
e. about 31.5% mass of l-carvone, about 30.3% mass of d-limonene, about 2.4% mass of 3-octonol, about 3% mass of dihydrocarvone, about 1.3% mass of menthone, and less than about 1% of 1,8-cineole.

\* \* \* \* \*